United States Patent
Narwani

[11] Patent Number: 5,881,422
[45] Date of Patent: Mar. 16, 1999

[54] TONGUE CLEANING DEVICE

[76] Inventor: Sharmine Narwani, 2141 Wyoming Ave., NW., No. 42, Washington, D.C. 20008

[21] Appl. No.: 800,180

[22] Filed: Feb. 13, 1997

[51] Int. Cl.[6] .............................. A47L 13/02; A46B 9/04
[52] U.S. Cl. ...................... 15/111; 15/236.01; 15/236.07
[58] Field of Search .................................. 15/111, 167.1, 15/236.01, 236.07; 606/161; 132/73, 73.5, 75.6, 321

[56] References Cited

U.S. PATENT DOCUMENTS

| | | | |
|---|---|---|---|
| 410,476 | 9/1889 | Woodard | 15/111 |
| 1,312,653 | 8/1919 | Watrous | 132/75.6 |
| 1,741,143 | 12/1929 | Chin | 15/111 |
| 3,147,840 | 9/1964 | Brookhouser | 15/111 |
| 3,254,356 | 6/1966 | Xao | 15/111 |
| 4,455,704 | 6/1984 | Williams | 15/111 |
| 5,005,246 | 4/1991 | Yen-Hui | 15/111 |
| 5,224,501 | 7/1993 | McKenzie | 132/321 |
| 5,564,148 | 10/1996 | Prevost | 15/111 |

FOREIGN PATENT DOCUMENTS

| | | | |
|---|---|---|---|
| 0051949 | 5/1982 | European Pat. Off. | 15/111 |
| 425177 | 6/1911 | France | 132/73 |
| 13341 | of 1894 | United Kingdom | 15/111 |
| 17643 | of 1911 | United Kingdom | 15/111 |
| 240586 | 10/1925 | United Kingdom | 15/111 |

*Primary Examiner*—Randall E. Chin
*Attorney, Agent, or Firm*—Arent Fox Kinter Plotkin & Kahn, PLLC

[57] ABSTRACT

The invention is directed to a device for cleaning the tongue to maintain positive oral hygiene and to control the proliferation of bacteria, plaque, tongue debris and film and the like. The device is used to scrape the tongue to remove bacteria, tongue debris and film and other particular matter from the tongue. It can be easily rinsed and reused, and, because it is manufactured from plastic, is easy and inexpensive to manufacture.

1 Claim, 1 Drawing Sheet

TONGUE CLEANING DEVICE

BACKGROUND OF THE INVENTION

Brushing and flossing the teeth have for years been acknowledged as staples of a good oral hygiene regimen and vitally important in preventing bad breath because they are used to remove plaque and food particles from the teeth and in between teeth. Less commonly acknowledged is that the presence of bacteria and other microorganisms and particulate matter on the tongue can also make a significant contribution to oral malodors in both periodontally-diseased and healthy persons. Studies have determined that sixty percent (60%) of the volatile sulfur compounds that cause bad breath are found on the tongue. Other causes of oral malodors include sinus infections, digestive problems, smoking, and eating and drinking of odorous foods such as onions, garlic, coffee, etc. Even the healthiest tongues will, on occasion, have a film of odorous debris that needs to be removed. Therefore, dentists frequently advise their patients to "brush their tongues" as a remedy. This activity, however, can be abrasive to the tongue and is largely ineffective.

Other devices have also been used to remove deposited matter from interdental areas, such as water jets. These devices, however, do not prevent the formation of plaque and remove only some of the sources of mouth odor and do not address the bacteria and debris formed on the tongue.

There have also been prior tongue cleaning devices. Prior tongue cleaning devices have been awkward and difficult to use because of odd shapes and can sometimes initiate the gagging reflex of the user, such as that disclosed in U.S. Pat. No. 5,061,272 to Reese which discloses a tongue cleaning device with an arc-shaped section used to scrape. Prior tongue cleaning devices have also been unacceptable because some have been harsh or abrasive to the tongue of the user, such as the tongue cleaning device disclosed in U.S. Pat. No. 2,543,999 which includes tongue surface abrading means. Also, some prior tongue cleaning devices that collect and trap tongue debris in a spoon-like receptacle or like repository are objectionable because they are quite unhygienic.

Thus, prior devices used to clean the tongue have not been commercially successful.

SUMMARY OF THE INVENTION

It is therefore an object of the present invention to provide an inexpensive, easily manufactured, tongue cleaning device for the effective removal of bacteria, tongue debris and film and other odor causing matter from the tongue.

It is a further object of the present invention to provide a tongue cleaning device which is not abrasive to the tongue.

It is an additional object of the present invention to provide a tongue cleaning device which is easy to clean after use and which can be used for multiple uses for at least as long a period as a standard toothbrush is used before disposal.

It is yet another object of the present invention to provide a tongue cleaning device which can be stored in a standard toothbrush holder.

It is a further object of the present invention to provide a tongue cleaning device which can be attached to a standard toothbrush.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purposes of the invention, as embodied and broadly described herein, the present invention is directed to a tongue cleaning device to remove bacteria, tongue debris and film and the like from the surface of the tongue comprising a planar, elongated member of relatively uniform width and thickness throughout the length of the member, said member being comprised of flexible material thereby permitting the planar, elongated member to be grasped by a user thereby to flexibly scrape the user's tongue with the device.

DETAILED DESCRIPTION OF THE PREFERRED EMBODIMENTS OF THE PRESENT INVENTION

Figure 1:
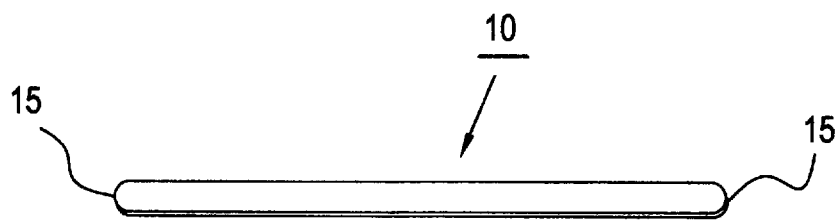
FIG. 1 illustrates a top view of the tongue cleaning device in accordance with the present invention.

Reference will now be made in detail to the present preferred embodiments of the invention, examples of which are illustrated in the accompanying drawings in which like reference characters refer to corresponding elements.

The present invention is directed to a tongue cleaning device which is inexpensive to manufacture, easy to use and clean and is effective for cleaning the tongue.

Figure 2:
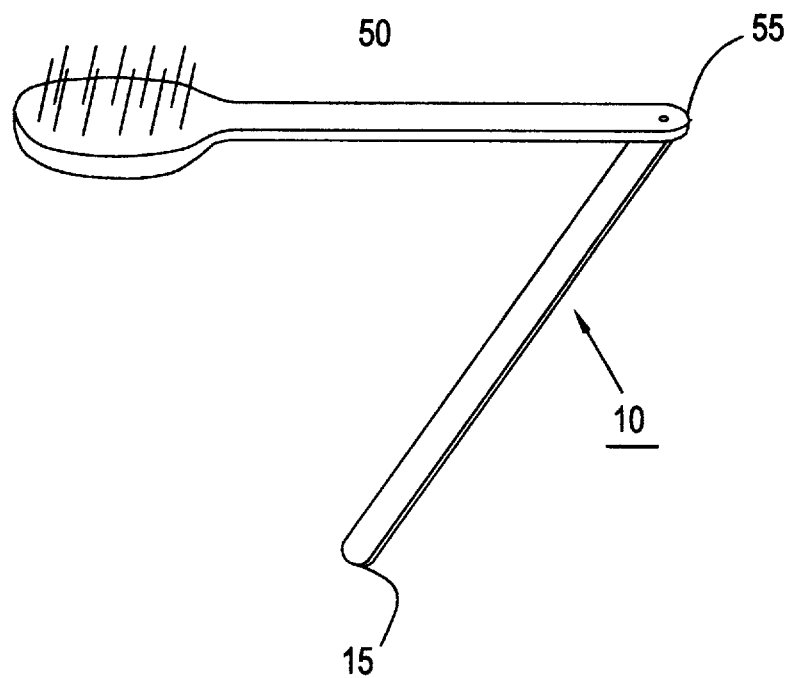
FIG. 2 illustrates a top view of the tongue cleaning device of FIG. 1 wherein the device is pivotally attached to a standard toothbrush.

The tongue cleaning device 10 as shown in FIG. 1 is comprised of a planar, elongated member, approximately 7¾ inches in length, approximately ¼ inch in width and approximately 0.013 to 0.018 inches in thickness. The length, width and thickness of device 10 can be varied, however, depending on user and manufacturer preferences. The device 10 is rounded on each end 15 as shown. As shown in FIG. 2, the device 10 can be pivotally attached to toothbrush 50 at attachment point 55, thereby enabling a user to have ready access to all needed dental and oral hygiene implements.

The device 10 can be manufactured from a polyvinyl chloride/polyethylene (PVC/PE) co-polymer type plastic and/or other similar plastics. Because of the inexpensive nature of this material, the device 10 can be manufactured from sheets of the polymer using a die to press out multiple devices 10. The ease of manufacture further contributes to the relative inexpensive nature of the device 10. Because the device 10 can be manufactured from polymers, it can be personalized by manufacturing it in different solid colors or with different designs imprinted thereon such as stars, stripes, etc. This personalization helps a person in a household distinguish his/her tongue cleaning device from that of another member of the household.

The user of device 10 would hold device 10 with both hands in a slightly flexed fashion. The user will open his/her mouth and extend his/her tongue therefrom and scrape the tongue by moving device 10 across the tongue. When particulate matter builds up on the device 10 from the scraping, device 10 can be rinsed to remove the particulate matter and the user may commence additional scraping.

Device 10 can be re-used for months following rinsing with soap and water between each scraping. Thus, device 10 is easier to clean than prior tongue cleaning devices that collect and trap tongue debris in a spoon-like receptacle or like repository which would require the user to ensure that the deposited materials were thoroughly rinsed from the receptacle such as by cleaning in a dishwasher.

Alternatively, device 10 can be comprised of wood or can be formed of stainless steel or other suitable rust-resistant steel alloys. The preferred embodiment is plastic, however, since wood may be more abrasive to the tongue and users experience greater discomfort when wood or stainless steel implements are inserted into the mouth since such materials can be more awkward and intrusive. The wood embodiment of the tongue cleaning device of the present invention would require a veneer coating to enhance the smoothness of the surface and to minimize splinters. The wood and steel embodiments would be of the same relative dimensions as the plastic embodiment.

The device 10 of the present invention is easy to use and less abrasive than using a toothbrush or prior tongue cleaning devices with abraded surfaces. Also, since it is small and flexible, there is less likelihood that a user will gag than with prior awkwardly-shaped devices. And, as discussed above, the tongue cleaning device of the present invention is more easily cleaned than prior devices.

It will be apparent to those skilled in the art that various modifications and variations can be made in the apparatus of the present invention without departing from the scope or spirit of the invention. Thus, it is intended that the present invention cover the modifications and variations provided they come within the scope of the appended claims and their equivalents.

What is claimed is:

1. A tongue cleaning device to remove bacteria, tongue debris and film from the surface of the tongue comprising:

a planar, elongated member of relatively uniform width and thickness throughout the member, said planar, elongated member being comprised of flexible material, thereby permitting said planar, elongated member to be grasped by a user at both ends thereby to flexibly scrape the user's tongue with said device, wherein said device is approximately 7¾ inches in length and ¼ inch in width with a thickness ranging from 0.013 to 0.018 inches and is comprised of a wood material with a veneer coating.

* * * * *